United States Patent [19]

Goel

[11] Patent Number: 4,833,273

[45] Date of Patent: May 23, 1989

[54] PROCESS FOR THE RESOLUTION OF 1-AMINOINDANES

[75] Inventor: Om P. Goel, Ann Arbor, Mich.

[73] Assignee: Warner-Lambert Company, Morris Plains, N.J.

[21] Appl. No.: 824,988

[22] Filed: Feb. 3, 1986

[51] Int. Cl.$^4$ .............................................. C07C 57/00
[52] U.S. Cl. ................................... 564/304; 562/401; 562/446; 564/428; 260/501.11
[58] Field of Search ............... 562/401, 446, 428, 304; 260/501.11

[56] References Cited

U.S. PATENT DOCUMENTS

| | | | |
|---|---|---|---|
| 3,028,430 | 4/1962 | Gillingham | 564/304 X |
| 3,167,566 | 1/1965 | Overby | 564/304 X |
| 3,734,952 | 5/1973 | Krubiner | 562/401 X |
| 3,919,316 | 11/1975 | Molloy | 564/428 |
| 3,969,397 | 7/1976 | Kaiser et al. | 564/304 X |
| 4,132,737 | 1/1979 | Molloy | 564/428 |
| 4,501,735 | 2/1985 | Trivedi et al. | 514/46 |

OTHER PUBLICATIONS

Bull. Chim. & Farm. 115: 489–500 (1976) translated.

*Primary Examiner*—Robert V. Hines
*Attorney, Agent, or Firm*—Elizabeth M. Anderson

[57] ABSTRACT

An improved process for the resolution of 1-aminoindanes into the R-isomer on a large scale is described. The resolving agent used in the process is R-N-acetyl-3,4-dimethoxyphenylalanine. The process is of intermediates in the production of certain adenosines and their pharmaceutically acceptable acid addition salts. The adenosines have desirable central nervous system and cardiovascular activities such as antipsychotic, sedative, antihypertensive, and antianginal.

2 Claims, No Drawings

PROCESS FOR THE RESOLUTION OF 1-AMINOINDANES

BACKGROUND OF THE INVENTION

The process of the present invention is an efficient method of resolving 1-aminoindanes into the R-isomer. The process is a simple method which gives high yields of the desired isomer.

In contrast the method in the literature gives a low yield. That resolution uses N-acetylleucine as the resolving agent and uses an aqueous solution. In 100 consecutive crystallizations of the salt obtained by combining equimolar quantities of DL-1-aminoindane and L-(−)-N-acetylleucine it was possible to obtain the R(−)-1-aminoindane L-(−)-N-acetylleucine from which R(−)-1-aminoindane and the R(+) hydrochloride were obtained. Low yield prompted attempts to recover and fractionally crystallize the salts present in the mother liquors of the resolution. *Bull Chim e Farm* 115: 489–500 (1976).

In the present invention the resolving agent used is R-N-acetyl-3,4-dimethoxyphenylalanine which is disclosed in U.S. Pat. No. 3,734,952 but not used as a resolving agent.

The process of the present invention may be used for producing intermediates in the synthesis of indanyladenosines which compounds are described in U.S. Pat. No. 4,501,735 herein incorporated by reference.

The present process gives greatly improved yield, 83% yield of R(−)-1-aminoindane compared to very low yields in the process described above.

DETAILED DESCRIPTION

The present invention is a greatly improved process for the resolution of 1-aminoindanes into the R-isomer. These are intermediates in the synthesis of indanyladenosines of the formula

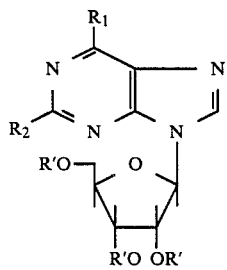

I where $R_1$ is of the formula

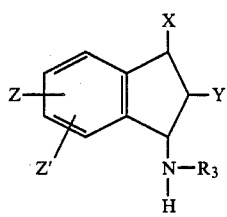

II wherein X is hydrogen, lower alkyl or lower alkyl terminally substituted by hydroxy, lower alkoxy or carboxyl, or where R is hydrogen, lower alkyl, lower alkanoyl or benzoyl, phenyl or phenyl substituted by halogen, hydroxy, lower alkoxy or trifluoromethyl; Y is hydrogen, lower alkyl or lower alkyl substituted by hydroxy, lower alkoxy, OR where R is hydrogen, lower alkyl, lower alkanoyl or benzoyl; Z and Z' are independently hydrogen, halogen, nitro, trifluoromethyl, lower alkyl, hydroxy, or lower alkoxy; $R_3$ is hydrogen or lower alkyl; R' is hydrogen, acetyl or benzoyl, $R_2$ is hydrogen or halogen, and the diastereomers or mixtures thereof, or a pharmaceutically acceptable acid addition salt thereof.

In the compounds of Formula I and II, the term lower alkyl is meant to include a straight or branched alkyl group having from one to six carbon atoms such as, for example, methyl, ethyl, propyl, isopropyl, butyl, sec-butyl, isobutyl, tertiarybutyl, amyl, isoamyl, neopentyl, hexyl, and the like.

Lower alkoxy is O-alkyl of from one to six carbon atoms as defined above for lower alkyl.

Halogen includes fluorine, chlorine, or bromine.

Compounds of Formula I are useful both in the free base form and in the form of acid addition salts.

Pharmaceutically acceptable salts are those derived from mineral acids such as hydrochloric acid and sulfuric acid, and organic acids such as methanesulfonic acid, benzenesulfonic acid, P-toluenesulfonic acid and the like.

The compound of Formula I may contain more assymmetric carbon atoms at the $N^6$ side chain.

Steps 3 and 4 of synthetic Scheme I are illustrative of the present invention.

The essential feature of present invention is the discovery that the resolving agent R-N-acetyl-3,4-dimethoxyphenylalanine obtained as a by product of the L-DOPA synthesis in U.S. Pat. No. 3,734,952, improves the resolution which results in greater overall yields of the desired enantiomeric form of the final product.

Step 1

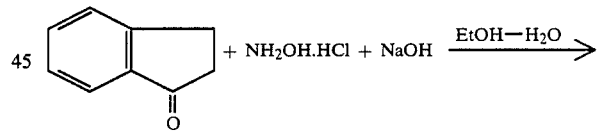

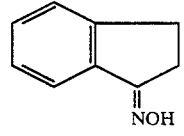

I

Step 2

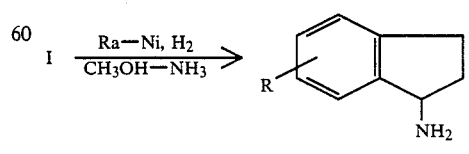

II (R,S)

Step 3

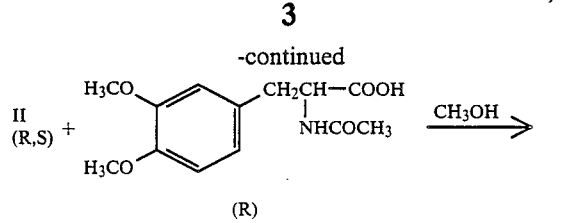

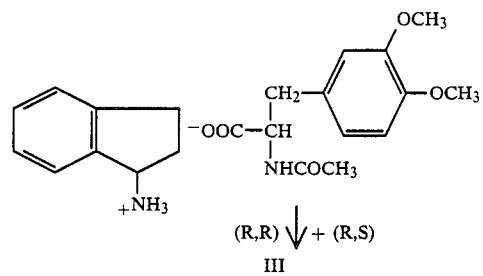

Step 4

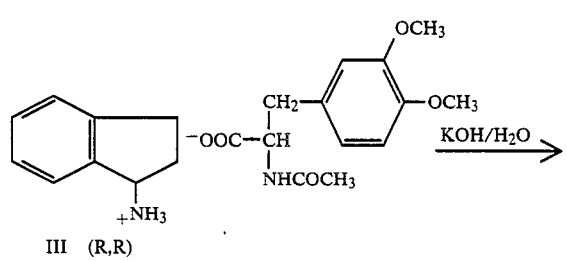

Step 5

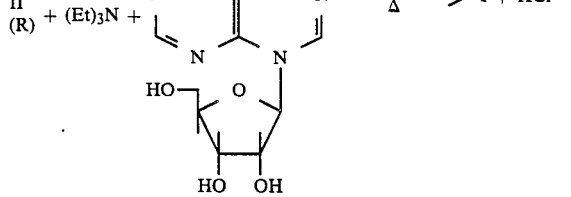

In Step 1 a 1-indanone is treated with a hydroxylamine and a base to produce a 1-indanone oxime. In Step 2 the oxime is hydrogenated to produce a corresponding primary amine, both R and S forms. In Step 3 the primary amine is then added to D-N-acetyl-3,4-dimethoxyphenylalanine in alcohol to produce the (R,R) and (R,S) salts of the primary amine. The (R,S) salt crystallizes first and the (R,R) salt is soluble. These are separated by filtration. The mother liquor, on concentrating and cooling precipitates the desired R,R isomer in high yield and optical purity. In Step 4 a solution of R,R isomer is treated with a base to produce the R form of the primary amine. In Step 5 the R primary amine is reacted with a tertiary amine and 6-chloropurineriboside to produce the adenosine compounds of Formula I of the present invention, for example, $N^6$-[1-(R)-indanyl]adenosine.

A preferred embodiment of the present invention is the use of methanol in Step 3 in producing the salts of the primary amine by which the R,S and R,R diastereomers are cleanly separated in high yield.

Another preferred embodiment is the use of the base potassium hydroxide for treating the filtrate.

Still another preferred embodiment is the process wherein the R form of Compound II in which X, Y, Z, and Z' are hydrogen is produced.

A particular preferred embodiment is the process whereby the compound of Formula I is $N^6$-[1-(R)-indanyl]adenosine or a pharmaceutically acceptable salt thereof which is obtained by the process wherein the resolving agent is R-N-acetyl-3,4-dimethoxyphenylalanine.

The compounds of Formula 1 have been found to possess differing affinities at adenosine receptors. These compounds are active in animal tests which are predictive of neuroleptic activity for the treatment of major psychoses such as schizophrenia. These compounds also have sedative and hypnotic properties and, as such, are useful for the treatment of sleep disorders.

Additionally, these compounds are useful as antihypertensive agents for the treatment of high blood pressure. They also increase coronary blood flow and as such are useful in the treatment of angina and myocardial ischemia.

The following examples are illustrative of the invention but are not meant to limit the invention in any way.

EXAMPLE 1

Preparation of 1-Indanone Oxime

In a 12 l four-necked flask fitted with a mechanical stirrer, a reflux condenser and a thermometer was placed 3.6 l of deionized water. Hydroxylamine hydrochloride was added. A clear, colorless solution formed (pH 2.5) to which was added 475 ml of 50% sodium hydroxide which had been diluted to 2.4 l with deionized water (pH 6.2). 1-Indanone was dissolved in 2.4 l of 3A anhydrous ethanol and added to the flask. The slightly turbid solution was heated at reflux for 15 minutes. A white solid started to precipitate at 39° C. The mixture was cooled to room temperature and then in an ice-water bath. The product was filtered off and washed with three 2 l portions of chilled water. The product was dried in a vacuum oven at 46° C. A white fluffy solid was obtained.

Weight=522.4 g
Yield 98.6%
mp 142°–144° C.

HPLC (18170X142A): 99.5%
IR (KBr) N 1841.950, satisfactory
NMR (d$_6$ DMSO) X 284.A883, satisfactory
Microanalysis: Calcd. for C$_9$H$_9$NO: C, 73.45; H, 6.16; N, 9.52. Found: C, 73.33; H, 6.21; N, 9.50

EXAMPLE 2

Preparation of 1-Aminoindane

The oxime (160 g, 1.087 mole) was dissolved in cold 1.6 l of methanol containing 16% of anhydrous ammonia. Raney nickel catalyst (12 g) was added and the mixture hydrogenated at a constant pressure of 50 psi. A nearly theoretical amount of hydrogen had been absorbed after 24.5 hours. The temperature range during hydrogenation was 15°–40° C. The filtered methanol solution was concentrated on the rotary evaporator (maximum bath temperature, 40° C.). The residue was distilled through a short four inch column packed with Goodloe teflon packing. The main fraction of 125 g was collected at 57° C. (0.35 mm).

Yield 86.4%
GC (18096X135) 99.3%
HPLC (18170X146C) 99.6%

EXAMPLE 3

Resolution of (R,S) 1-Aminoindane into the (R,R) and (R,S) Salts of R-N-acetyl-3,4-dimethoxyphenylalanine To a 5 l, three-necked flask fitted with a mechanical stirrer, a nitrogen blanket adapter, a reflux condenser and a thermometer was added D-N-acetyl-3,4-dimethoxyphenylalanine and 2.5 l of methanol. The solution was heated to 60° C. and a solution of (R,S)-1-aminoindane in 250 ml of methanol was added slowly to keep refluxing under control. A white solid precipitated which was the (R,S) salt. The (R,R) salt remained in solution. After stirring and cooling to room temperature, the mixture was stored in the cold room overnight. The solid was filtered off, washed with small portions of cold methanol and dried in a vacuum oven at 10 mm pressure for 24 hours. There was obtained 200 g (97.5%) of the R,S salt.

mp 212.5°–214.5° C.
$[\alpha]_D^{23} = -53.1°$ (1.03% in CH$_3$OH)
Microanalysis: Calcd. for C$_{22}$H$_{28}$N$_2$O$_5$: C, 65.98; H, 7.05; N, 6.99. Found: C, 65.96; H, 7.01; N, 7.11

The filtrate from above was charcoaled, filtered, and reduced in volume to 1.8 l on a rotary evaporator. A small amount of precipitate was filtered off, weight=1.54 g, mp 189°–190° C.

The filtrate was stored in the refrigerator overnight. The white solid was filtered and washed with three 50 ml portions of cold methanol. The product was dried in a vacuum oven at 68° C. to give 140 g of the R,R isomer.

Yield 68.2%
mp 194.5°–195.8° C.
$[\alpha]_D^{23} = -52.8°$ (1.09% in methanol)

The filtrate from above was concentrated to approximately 900 ml and further stored in the refrigerator overnight to afford a second crop of the R,R isomer.

Weight=29.9 g
Yield 14.6%
mp 191°–193° C.
$[\alpha]_D^{23} = -49.2°$
Microanalysis: Satisfactory Total yield of first and second crops=82.8%. Both first and second crops were combined for subsequent reactions.

EXAMPLE 4

Preparation of R-(−)-aminoindane

The R-1-aminoindane free base was isolated by dissolving 187 g of the R,R salt in 1.4 l of deionized water, and adding sufficient 50% KOH solution to reach a pH of 12.9. The mixture was extracted with three 1.4 l portions of diethyl ether. The combined extracts were dried over anhydrous MgSO$_4$ and the solvent removed as much as possible on a rotary evaporator (bath temperature 36° C.). The vacuum on the flask was released with nitrogen to avoid the carbonate formation. A 0.5 ml portion of R-1-aminoindane obtained in this manner was converted to the hydrochloride salt for identification purpose.

mp 237°–238° C.
$[\alpha]_D^{23} = +3.5°$ C. (1% solution in methanol)
Microanalysis: Calcd. for C$_9$H$_{11}$N.HCl: C, 63.72; H, 7.13; N, 8.26. Found, C, 63.83; H, 7.21; N, 8.25

The residual liquid was diluted with 200 ml of anhydrous 3A ethanol and kept under a nitrogen atmosphere.

EXAMPLE 5

Preparation of N$^6$-[1-(R)-indanyl]adenosine

A 5 l, four-necked flask was fitted with a sealed mechanical stirrer, a thermometer, a reflux condenser, and a N$_2$ blanket adapter. To this flask was added 156 ml of 3A anhydrous ethanol, 126.8 g of 6-chloropurineriboside, 65.4 ml of dry triethylamine and the alcoholic solution of R-1-aminoindane obtained above. the slightly green suspension was heated at reflux for 24 hours, cooled to room temperature, and then stored in the refrigerator overnight.

The product was collected by filtration, washed with three 100 ml portions of cold 3A alcohol, and dried in a vacuum oven at a maximum temperature of 88° C. There was obtained 121.8 g of a white crystalline solid.

Yield 74.9%
mp 186.7°–188.5° C. (clear melt)

A mixture melting point with an authentic sample was underpressed.

HPLC (18643X2C) 99.7%
IR (KBr) N 1842 482, satisfactory
NMR (d$_6$ DMSO 11840772 and D$_2$O exchange), satisfactory
Rotation A-26628 $[\alpha]_D^{23} = +4.3°$ (1.07% in DMF)
Water (K-F) None
Microanalysis: Calcd. for C$_{19}$H$_{21}$N$_5$O$_4$: C, 59.52; H, 5.52; N, 18.27. Found, C, 59.21; H, 5.56; N, 18.62

I claim:

1. The process wherein the R form of the compound of formula

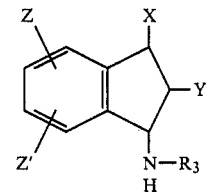

wherein X, Y, Z, and Z' are hydrogen and $R_3$ is hydrogen or lower alkyl which comprises
(a) reacting R-N-acetyl-3,4-dimethoxyphenyl alanine in an alcohol with an (R,S) mixture of a compound of the above formula as defined above;
(b) removing the precipitated (R,S) salt;
(c) concentrating the filtrate containing the (R,R) salt, treating with base, separating and isolating according to known means the desired R isomer of the compound above.

2. The process according the claim 1 wherein $R_3$ is hydrogen.

* * * * *